US00PP21448P3

(12) United States Plant Patent
Bautista

(10) Patent No.: US PP21,448 P3
(45) Date of Patent: Nov. 2, 2010

(54) ***ORNITHOGALUM* PLANT NAMED 'DAMASCUS'**

(50) Latin Name: *Ornithogalum thrysoides Jasq.*
Varietal Denomination: Damascus

(75) Inventor: Rodolfo Valdoz Bautista, Half Moon Bay, CA (US)

(73) Assignee: Bay City Flower Company, Inc., Half Moon Bay, CA (US)

( * ) Notice: Subject to any disclaimer, the term of this patent is extended or adjusted under 35 U.S.C. 154(b) by 0 days.

(21) Appl. No.: 12/315,280

(22) Filed: Dec. 1, 2008

(65) Prior Publication Data

US 2010/0138970 P1 Jun. 3, 2010

(51) Int. Cl.
*A01H 5/00* (2006.01)

(52) U.S. Cl. ..... Plt./462

(58) Field of Classification Search ..... Plt./462
See application file for complete search history.

(56) References Cited

U.S. PATENT DOCUMENTS

PP12,850 P2 * 8/2002 Griesbach et al. ..... Plt./462
PP13,200 P2 * 11/2002 Griesbach et al. ..... Plt./462

* cited by examiner

*Primary Examiner*—June Hwu
(74) *Attorney, Agent, or Firm*—James R. Cypher; Charles R. Cypher

(57) ABSTRACT

A new and distinct cultivar of *Ornithogalum thyrsoides* Jacq. named 'Damascus' originated as a controlled cross between the commercial cultivar *Ornithogalum thyrsoides* Jacq. 'Chesapeake Snowflake' and an unnamed *Ornithogalum thyrsoides* Jacq. cultivar. The cultivar 'Damascus' has R.H.S. 155 A (white group) tepals at maturity and is distinguished from other similar cultivars of which the inventor is aware by its erect racemes, wide leaves that lay flat and its suitability for growth in pots.

5 Drawing Sheets

Botanical classification: *Ornithogalum thyrsoides* Jasq. 'Damascus'.

Variety denomination: 'Damascus'.

BACKGROUND OF THE INVENTION

This invention relates to a new and distinct cultivar of the Lilaceae family. The botanical name of the plant is *Ornithogalum thyrsoides* Jasq. 'Damascus'.

The new cultivar originated as a seedling from a controlled cross between the commercial variety *Ornithogalum thyrsoides* 'Chesapeake Snowflake' (U.S. Plant Pat. No. 13,200) and an unnamed *Ornithogalum thyrsoides*. 'Chesapeake Snowflake' was the seed parent. 'Chesapeake Snowflake' is the progeny of the commercial variety 'Bok Bay'.

The new variety 'Damascus' is differentiated from its seed parent and other commercial varieties known to the inventor as shown in the table below.

TABLE 1

| | New Variety 'Damascus' Ser. No.: 12/315,280 | New Variety 'Bethlehem' Ser. No.: 12/315,215 | 'Chesapeake Snowflake' U.S. Plant Pat. No. 13,200 (seed parent) | 'Chesapeake Starlight' U.S. Plant Pat. No. 12,850 |
|---|---|---|---|---|
| Rachis/ Raceme height | 40 cm | 43 cm | 20-30 cm | 55-60 cm |
| Rachis color | R.H.S. 146B | R.H.S. 146A | Unknown | Unknown |
| Reflexed leaves | Yes | Yes | Unknown | Unknown |
| Leaf color | R.H.S. 147B | R.H.S. 146A | R.H.S. 143B | R.H.S. 143B |
| Floret diameter | 65 mm | 70 mm | 50-60 mm | 35-40 mm |
| Tepal height | 28 mm | 36 mm | 20-25 mm | 20 mm |

TABLE 1-continued

| | New Variety 'Damascus' Ser. No.: 12/315,280 | New Variety 'Bethlehem' Ser. No.: 12/315,215 | 'Chesapeake Snowflake' U.S. Plant Pat. No. 13,200 (seed parent) | 'Chesapeake Starlight' U.S. Plant Pat. No. 12,850 |
|---|---|---|---|---|
| Tepal Color | R.H.S. 155A | R.H.S. 155C | R.H.S. 155A-D | R.H.S. 155A-D |
| Tepal Spot Color | R.H.S. 152B | R.H.S. 152A | R.H.S. 147A | R.H.S. 152A |

The new variety was first noticed, because of its erect, but relatively short racemes and its smaller flowers.

The new cultivar 'Damascus' has been asexually reproduced through three generations under controlled environmental conditions at a nursery in Half Moon Bay, Calif. under the direction of the inventor with its distinguishing characteristics remaining stable.

'Damascus' is distinguished from other *Ornithogalum thyrsoides* varieties of which the inventor is aware by its relatively short, upright racemes, its less upright leaves, its suitability for growth in pots and its relatively smaller flowers.

Asexual reproduction was first accomplished when vegetative cuttings were taken from the initially selected plant. Examination of asexually reproduced, successive generations grown in a nursery at Half Moon Bay, Calif. show that the combination of characteristics as herein disclosed for 'Damascus' remains firmly fixed through three generations.

DESCRIPTION OF THE DRAWINGS

The accompanying drawings consist of color photographs that show the typical plant form, including the inflorescence, foliage, and sepals.

DESCRIPTION OF THE NEW PLANT

Figure 1:
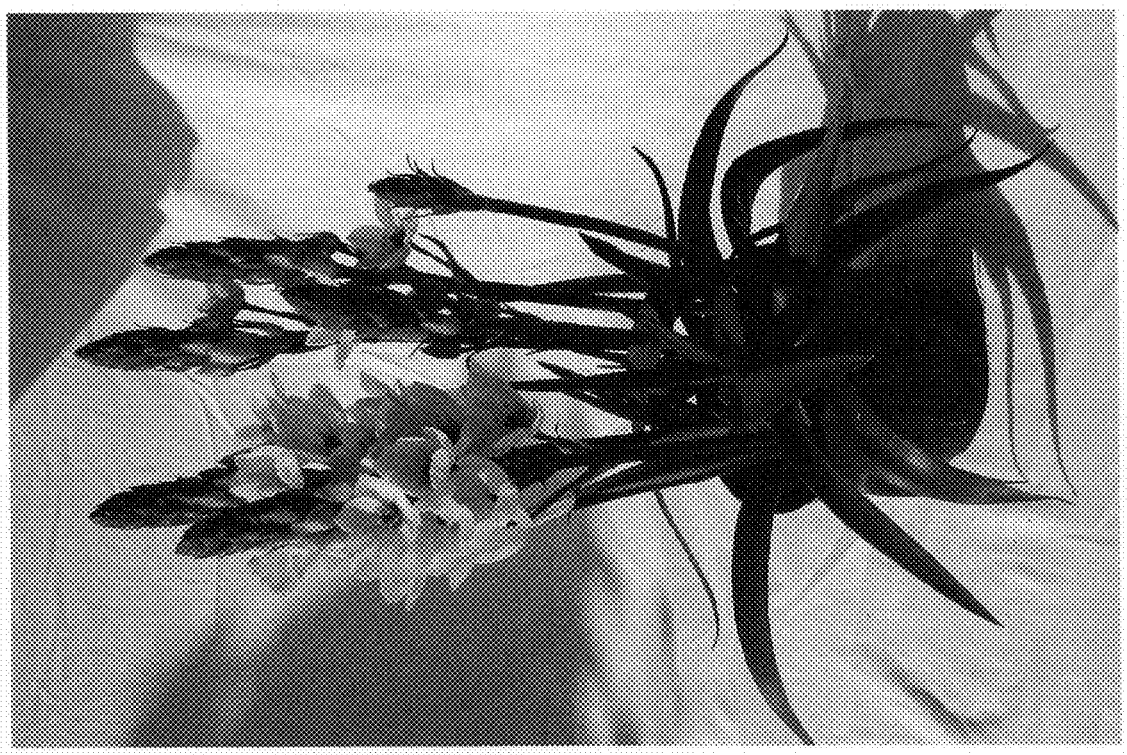
FIG. 1 is a view of the new variety showing its form, upright growth habit, dark green foliage, inflorescence, and non-pigmented tepals.
Figure 2:
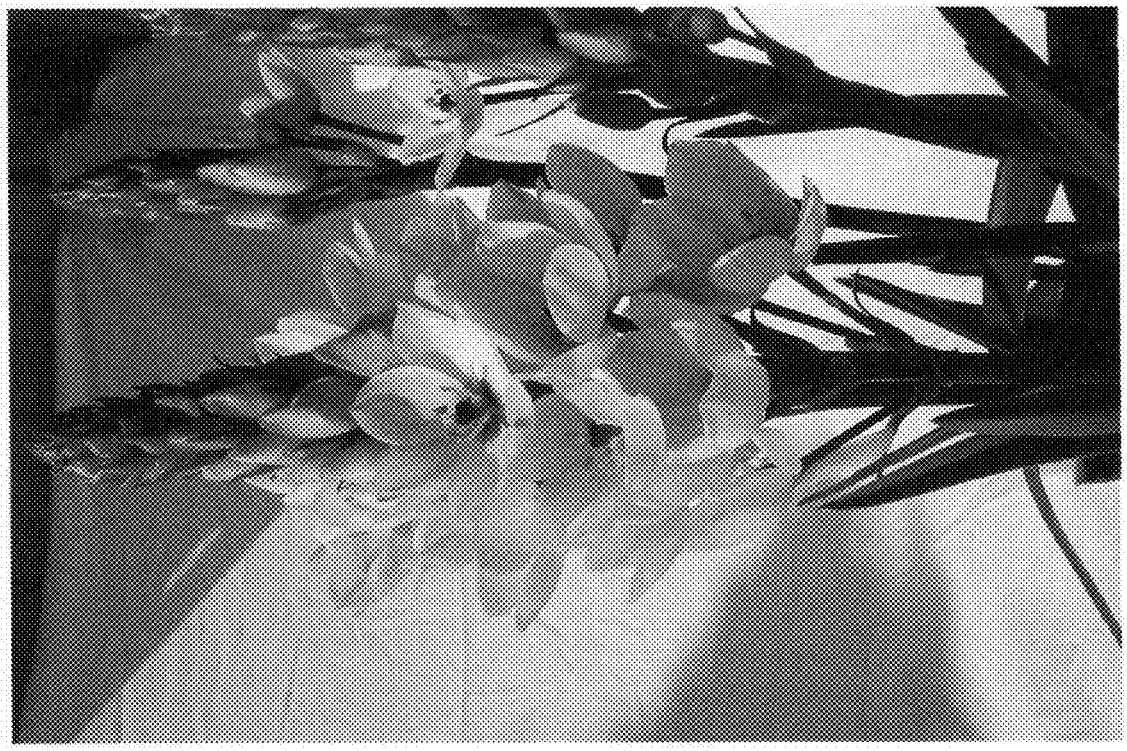
FIG. 2 is a view of the inflorescence of the new variety.
Figure 3:
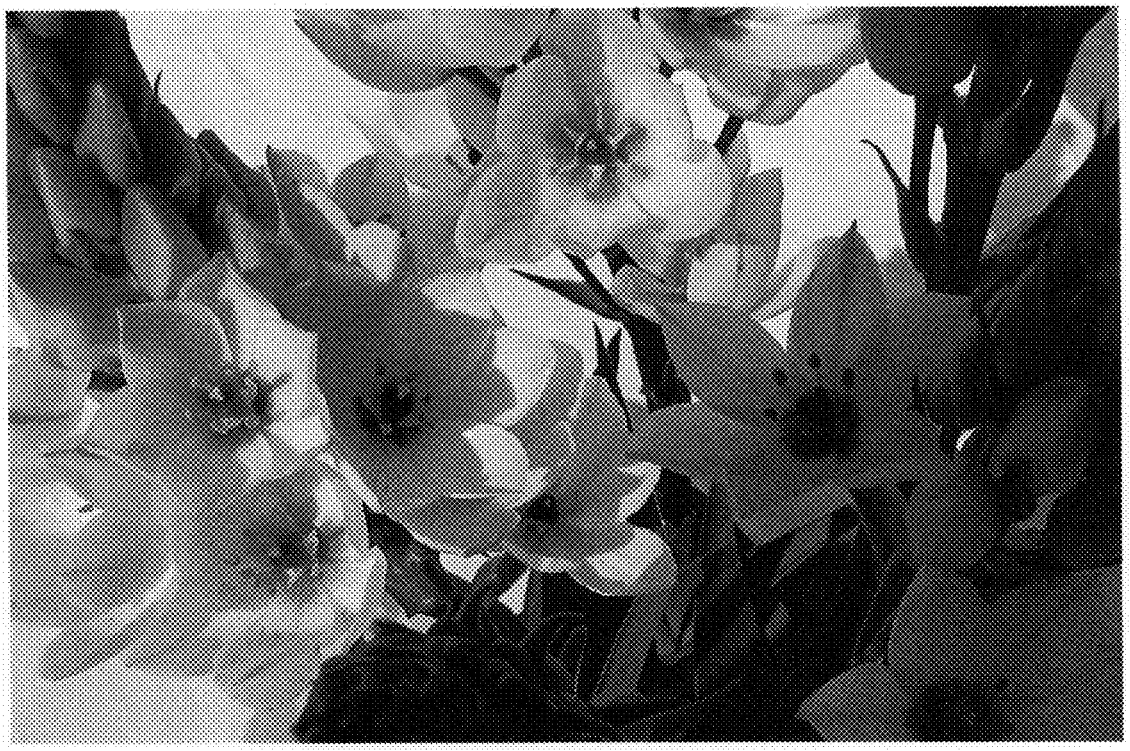
FIG. 3 is a close-up view of the inflorescence of the new variety, showing opened florets, and opening florets.
Figure 4:
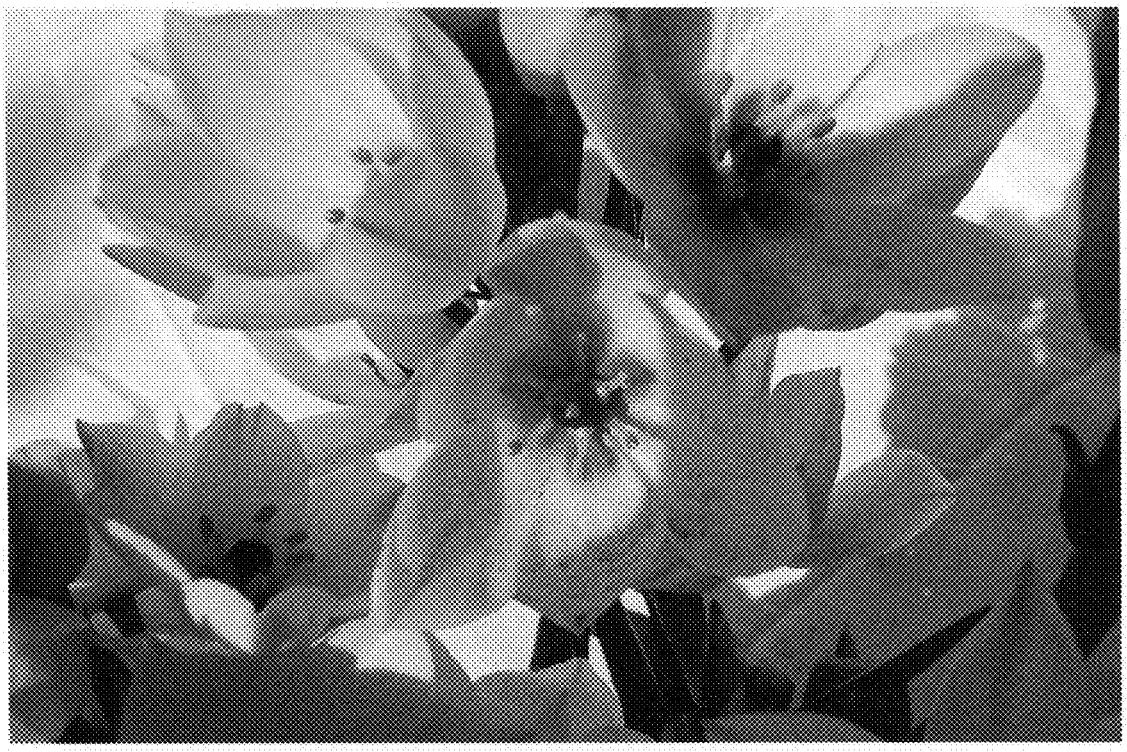
FIG. 4 is a close-up view of the inflorescence of the new variety, showing opened florets, and opening florets.
Figure 5:
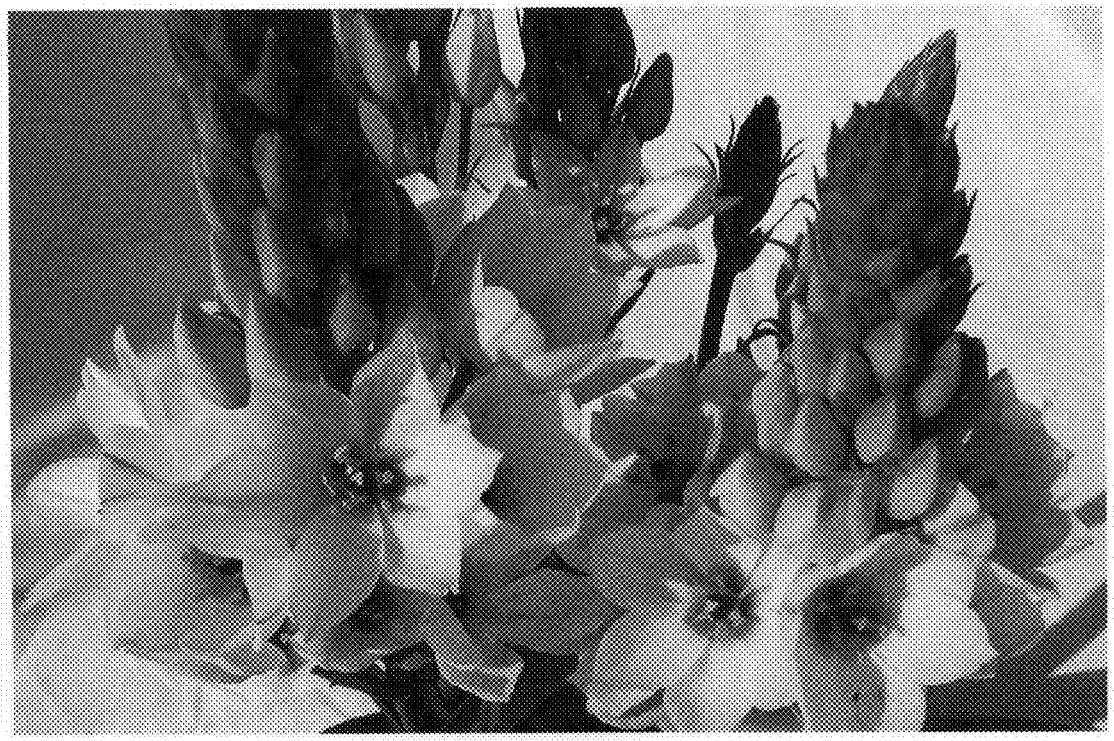
FIG. 5 is a top view of a number of inflorescences of the new variety.
Figure 6:
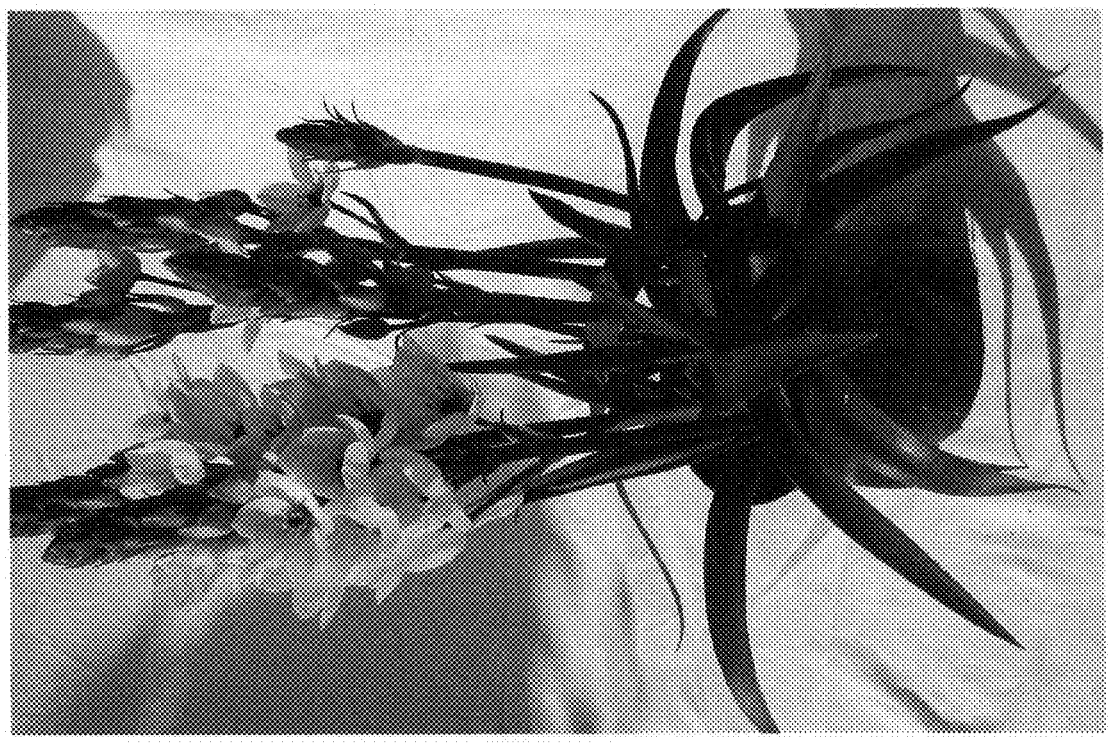
FIG. 6 is a view of the new variety.
Figure 7:
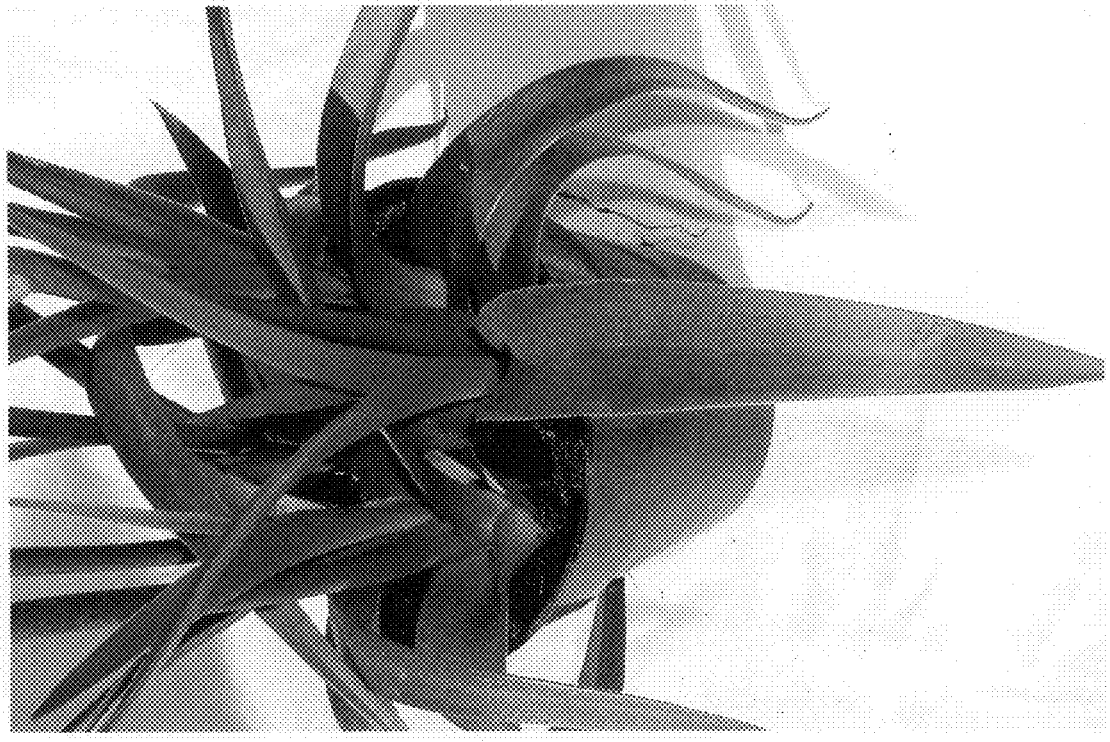
FIG. 7 is a view of the base of the new variety.
Figure 8:
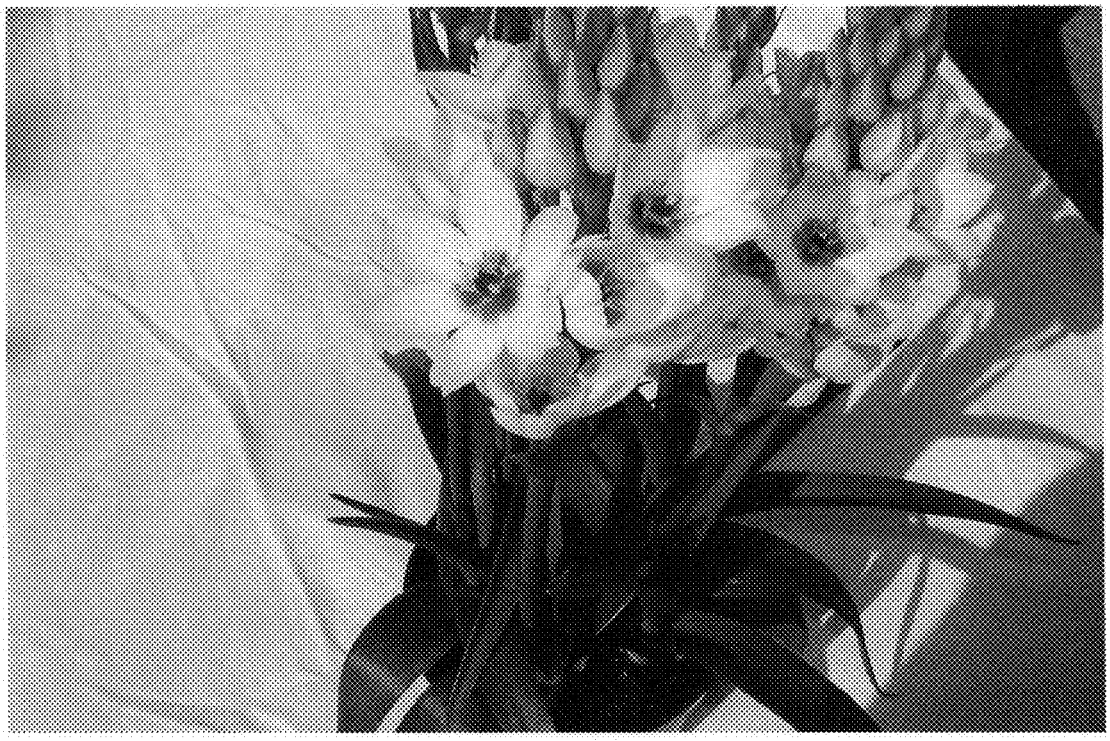
FIG. 8 is a view of the upper portion of multiple inflorescences of the new variety.
Figure 9:
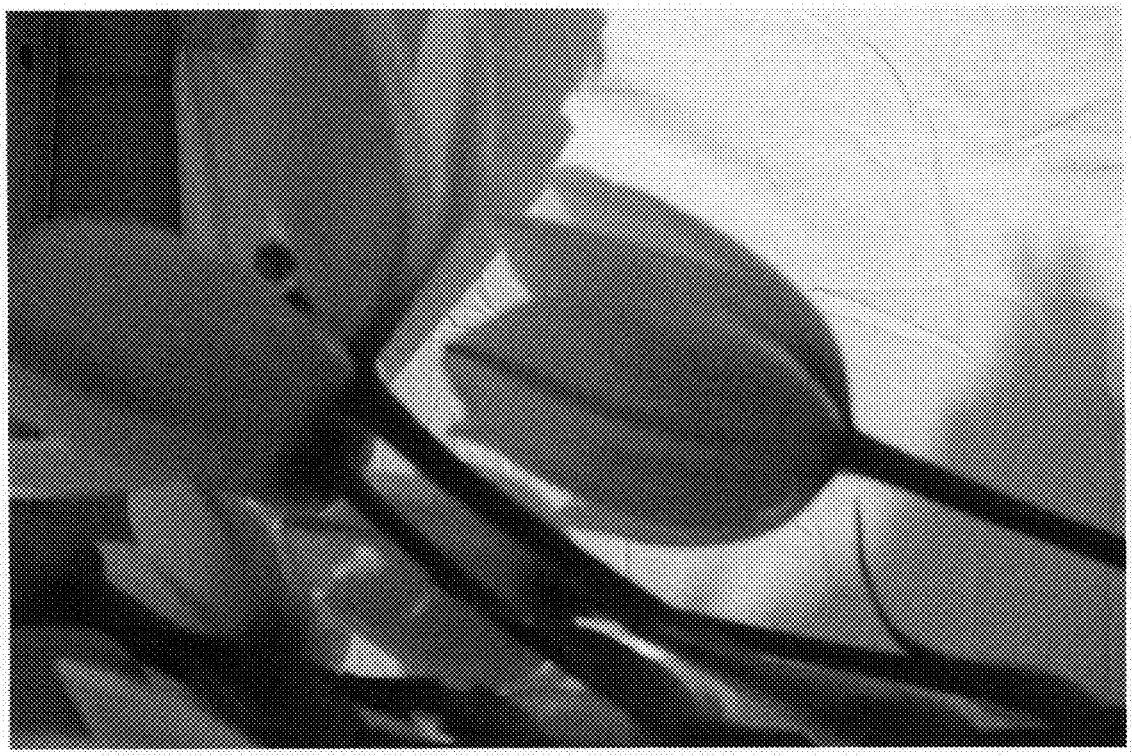
FIG. 9 is a close-up, side view of florets of the new variety.
Figure 10:
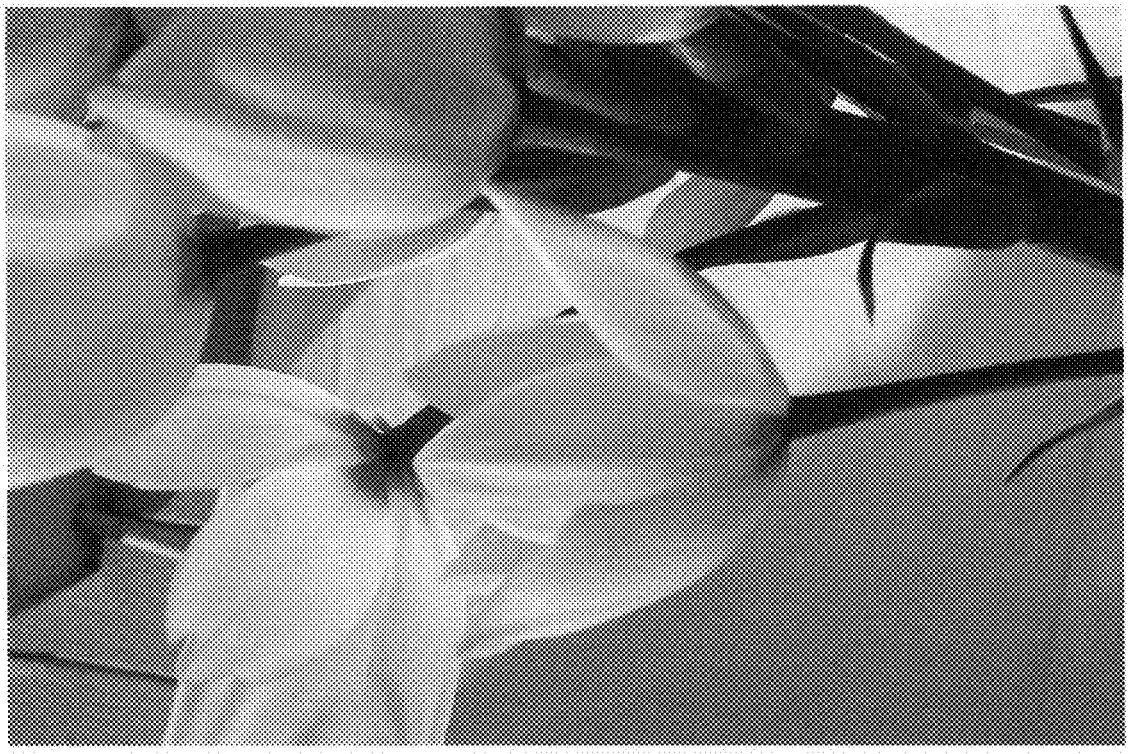
FIG. 10 is a close-up, side view of florets of the new variety.

The plants shown in the figures were grown in 6" pots and were approximately 7 months old. The plants were started in the green house for 20 to 25 weeks and then move outside.

'Damascus' has not been observed under all possible environmental conditions. The phenotype may vary significantly with variations in environment such as temperature, light intensity and day length. Color determinations were made with The Royal Horticultural Society (R.H.S.) Colour Chart.

THE PLANT

Origin: Controlled cross.

*Parents.*—*Ornithogalum thyrsoides* Jasq. 'Chesapeake Snowflake' U.S. Plant Pat. No. 13,200) and an unnanmed *Ornithogalum thyrsoides* Jasq.

*Botanic classification.*—*Ornithogalum thyrsoides* Jasq. 'Damascus'.

Form: Spreading basal leaves with upright inflorescences on tall rachis. A typical plant with a mature inflorescence that is ready for sale is approximately 40 cm high when grown in a 6" pot with appropriate soil amendments. Growth: Upright rachis with spreading leaves. Inflorescence is large and showy.

Rachis: The rachis is upright and glaucous. Its color is R.H.S. 146 B (yellow-green group) (younger) to R.H.S. 147 B (yellow-green group). Diameter: 7 mm. The length of the rachis to the first floret and bract pair is variable and ranges from 15 cm to 25 cm.

Foliage: Usually five leaves surround each rachis on a mature plant ready for commercial sale. Leaves are whorled at base of stem.

*Shape of leaf.*—Fleshy, varying from somewhat channeled to flat, lanceolate. Margins are entire. Apex is acute.

*Texture.*—Glaucescent.

*Color.*—Mature leaves are R.H.S. 147 B (yellow-green group) on both abaxial and adaxial surfaces. Large leaves are 27 cm long and 5 cm wide.

INFLORESCENCE

Form: Corymbose racemes. Indeterminate. Approximately 100 to 125 individual flowers (florets) per inflorescence on pedicels that elongate as the florets opens, and on average are as long as 50 mm for mature florets. Flowers do not produce a fragrance. Buds are predominately green—R.H.S. 146 B (yellow-green group, 1.2-1.5 cm tall and have diameter of 8 to 10 mm. The rachis for the inflorescence is strong and upright. The pedicels are predominately green—R.H.S. 146 B (yellow-green group) at maturity and globrous.

Size of inflorescence: Large. A typical inflorescence shown in the figures can be 17.5 cm high.

Shape: Basal florets opening first with pedicels that elongate that give the raceme a corymbose appearance as the inflorescence ages.

Appearance: Showy.

FLORETS

*General.*—The florets at the base of the inflorescence open first, and open more and more as the inflorescence ages. Florets are perfect and complete. Perianth is not keeled. Perianth can be hightly reflexed. Each floret is associated with a bract that can be as high as 50 mm and is same color as leaves—R.H.S. 147 B (yellow-green group). The bracts are lanecolate with narrowly acute apexes and are approximately 7 mm wide at their base. Perianth: There are 6 ovate tepals that are spotted at their base—R.H.S. 152 B (yellow-green group), but are predominately white on both their abaxial and adaxial surfaces—R.H.S. 155 A (white group) with the mid-vein showing on the abaxial surface—R.H.S. 145 A (yellow-green group). Floret diameter: 65 mm. Tepals of mature florets are typically 28 mm high, 18 mm wide, 4 mm wide at their attachment, and the spotted base is approximately 5 mm high and extends the width of the tepal at the base. Apex shape of the tepal is abruptly acuminate.

*Stamens.*—6 stamens (two sets of 3). Pollen is R.H.S. 14 A (yellow-orange group). Plant produces abundant pollen. Filament is flattened with alternate stamens having enlarged translucent wings. Filament is 3 mm wide at base and 10 mm high. Filaments with wings are 3 mm at their widest point. Anther is 2 mm high and basally attached. Filament is R.H.S. 155 A (white group. Anther is R.H.S. 146 B (yellow-green group) before opening to reveal pollen.

*Stigma.*—Generally, a three-pronged stigma on one pistil per floret. The style is 3 mm long. The stigma is approximately 2 mm long. Style and stigma are R.H.S. 155 A (white group).

*Ovary.*—The ovary is three-celled with axile placentae. The base of the ovary is R.H.S. 152 A (yellow-green group) and the top of the ovary is R.H.S. 166 A (greyed-orange group). The ovary is 6 mm high and has a diameter of 7 mm.

I claim:

1. A new and distinct *Ornithogalum* plant named 'Damascus' substantially as herein shown and described.

* * * * *